United States Patent
Elliott (10) Patent No.: US 9,877,719 B2
(45) Date of Patent: Jan. 30, 2018

(54) FASCIAL HARVESTER DEVICE

(71) Applicant: Mayo Foundation for Medical Education and Research, Rochester, MN (US)

(72) Inventor: Daniel S. Elliott, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 363 days.

(21) Appl. No.: 14/814,794

(22) Filed: Jul. 31, 2015

(65) Prior Publication Data

US 2016/0030041 A1     Feb. 4, 2016

Related U.S. Application Data

(60) Provisional application No. 62/032,841, filed on Aug. 4, 2014.

(51) Int. Cl.
| | |
|---|---|
| *A61B 17/32* | (2006.01) |
| *A61M 29/00* | (2006.01) |
| *A61B 17/072* | (2006.01) |
| *A61B 17/3205* | (2006.01) |
| *A61B 17/02* | (2006.01) |
| *A61B 17/00* | (2006.01) |

(52) U.S. Cl.
CPC ........ *A61B 17/072* (2013.01); *A61B 17/0218* (2013.01); *A61B 17/3205* (2013.01); *A61M 29/00* (2013.01); *A61B 2017/00353* (2013.01); *A61B 2017/00805* (2013.01); *A61B 2017/00969* (2013.01); *A61B 2017/320064* (2013.01)

(58) Field of Classification Search
CPC .................. A61M 29/00; A61M 29/02; A61M 2029/025; A61M 25/10; A61M 25/1002; A61M 2025/1004; A61M 25/104; A61B 17/10; A61B 17/105; A61B 17/115; A61B 17/1152; A61B 17/068; A61B 17/0682; A61B 17/0684; A61B 17/0686; A61B 2017/07285
See application file for complete search history.

(56) References Cited

U.S. PATENT DOCUMENTS

| | | | |
|---|---|---|---|
| 2001/0018596 A1* | 8/2001 | Selmon ................. | A61M 29/02 606/198 |
| 2008/0312686 A1* | 12/2008 | Ellingwood ....... | A61B 17/0057 606/219 |
| 2009/0234379 A1 | 9/2009 | Rehnke | |
| 2009/0234461 A1 | 9/2009 | Rehnke | |

* cited by examiner

*Primary Examiner* — Jonathan Miles
(74) *Attorney, Agent, or Firm* — Fish & Richardson P.C.

(57) ABSTRACT

This document provides devices and methods for harvesting tissue. For example, this document provides devices and methods for harvesting abdominal wall fascial tissue in a minimally invasive manner.

18 Claims, 5 Drawing Sheets

FASCIAL HARVESTER DEVICE

CROSS-REFERENCE TO RELATED APPLICATIONS

This application claims the benefit of U.S. Provisional Application Ser. No. 62/032,841, filed Aug. 4, 2014. The disclosure of the prior application is considered part of (and is incorporated by reference in) the disclosure of this application.

BACKGROUND

1. Technical Field

This document relates to devices and methods for harvesting tissue. For example, this document relates to devices and methods for harvesting abdominal wall fascial tissue in a minimally invasive manner.

2. Background Information

Fascia is a sheet or band of fibrous connective tissue that surrounds muscles, groups of muscles, blood vessels, or nerves. Fascia binds some structures together, while permitting others to slide smoothly over each other.

The rectus sheath is formed by the aponeuroses of the transversus abdominis and the external and internal oblique muscles. It contains the rectus abdominis and pyramidalis muscles. Below the rectus sheath are the following layers: (i) transverse fascia, (ii) extraperitoneal fat, and (iii) parietal peritoneum. The transverse fascia is a thin aponeurotic membrane that lies between the inner surface of the transversus abdominis muscle and the extraperitoneal fascia. The transverse fascia forms part of the general layer of fascia lining the abdominal parietes, and is directly continuous with the iliac and pelvic fasciae.

Stress urinary incontinence (SUI) affects 15-60% of women. It is a disorder that affects both young and elderly individuals. A pubovaginal sling is a procedure used to manage urinary incontinence. The procedure involves placing a band of sling material directly under the bladder neck (e.g., proximal urethra) or mid-urethra, which acts as a physical support to prevent bladder neck and urethral descent during physical activity. The sling also may augment the resting urethral closure pressure with increases in intra-abdominal pressure.

In some cases, surgeons use synthetic mesh sling to treat SUI. An alternative is construction of a sling from a piece fascia, such as from a strip of harvested abdominal wall fascia. This advantageously results in an all-natural and autologous sling that does not use any synthetic components. A minimally invasive technique for harvesting abdominal wall fascia would provide benefits to patients who are treated for SUI using the all-natural and autologous sling made of abdominal wall fascia.

SUMMARY

This document provides devices and methods for harvesting tissue. For example, this document provides devices and methods for harvesting a strip of abdominal wall fascial tissue in a minimally invasive manner.

In one implementation, a device for harvesting a rectus fascia strip from a patient in a minimally invasive manner includes: (a) a dilator including a working end, a grip end, and a shaft extending between the working end and the grip end, the working end being configured to dissect the rectus fascia; (b) a cutter-stapler, the cutter-stapler including a first arm and a second arm, distal ends of at least one of the first arm and second arm configured to cut and staple the rectus fascia in response to being actuated; and (c) a connection hub, the dilator being pivotable coupled to the connection hub, the first arm and the second arm being pivotable coupled to the connection hub.

Such a device for harvesting a rectus fascia strip from a patient in a minimally invasive manner may optionally include one or more of the following features. The working end may be generally cylindrical. The dilator may be pivotably coupled to the connection hub about a first pin. The dilator may be comprised of stainless steel. A proximal portion of the dilator may include a grip end configured for manual manipulation by a clinician. The first arm and the second arm may be pivotably coupled to the connection hub about a second pin. The dilator may be pivotably coupled to the connection hub about a first pin, the first arm and the second arm may be pivotably coupled to the connection hub about a second pin, and the first pin may be perpendicular to the second pin.

In another implementation, a method for harvesting a rectus fascia strip from a patient in a minimally invasive manner includes: incising an abdomen of the patient to create an incision; inserting a distal portion of a rectus fascia harvesting device through the incision; dilating, using the working end, the rectus fascia; actuating the rectus fascia harvesting device to position the rectus fascia between the distal ends of the first arm and second arm; actuating the rectus fascia harvesting device to install a plurality of staples and to cut the rectus fascia to create a strip of harvested rectus fascia; and removing the rectus fascia harvesting device and the strip of harvested rectus fascia from the patient. The rectus fascia harvesting device may comprise: (a) a dilator including a working end, a grip end, and a shaft extending between the working end and the grip end, the working end being configured to dissect the rectus fascia; (b) a cutter-stapler, the cutter-stapler including a first arm and a second arm, distal ends of at least one of the first arm and second arm configured to cut and staple the rectus fascia in response to being actuated; and (c) a connection hub, the dilator being pivotable coupled to the connection hub, the first arm and the second arm being pivotable coupled to the connection hub.

Such a method for harvesting a rectus fascia strip from a patient in a minimally invasive manner may optionally include one or more of the following features. The inserting may include positioning the working end and the distal ends of the first arm and the second arm on opposite sides of the rectus fascia. The inserting may include placing an entire length of the working end in contact with the rectus fascia. The actuating the rectus fascia harvesting device to position the rectus fascia between the distal ends of the first arm and second arm may include pinching the rectus fascia between the distal ends of the first arm and second arm. The strip of harvested rectus fascia may be about 1 cm to about 4 cm in width. The plurality of staples may be biodegradable.

Particular embodiments of the subject matter described in this document can be implemented to realize one or more of the following advantages. In some embodiments, the treatment of SUI and other conditions can be facilitated using the devices and methods provided herein. In some embodiments, abdominal wall fascial tissue to treat such conditions can be harvested in a minimally invasive fashion using the devices and methods provided herein. Those minimally invasive techniques can reduce recovery times, patient discomfort, and treatment costs. Further, the devices and methods disclosed herein provide benefits to patients who are treated for SUI by using an all-natural and autologous sling made of abdominal wall fascia, rather than a sling of synthetic mesh material.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document provides devices and methods for harvesting tissue. For example, this document provides devices and methods for harvesting a strip of abdominal wall fascial tissue in a minimally invasive manner.

The principles embodied in the devices and methods provided herein may also be applied in the context of devices and methods to harvest other types of tissues such as, but not limited to, skin-layer harvesting and muscle harvesting in which the harvested tissue needs to be elevated, transected and reapproximated.

The abdominal wall fascial harvesters provided herein are an intraoperative surgical device for the purpose of obtaining a small segment of rectus fascia. The devices are intended to simply, quickly, and with reduced morbidity harvest a small section of rectus wall fascial tissue to be used for the purpose of a minimally invasive transobturator sling.

In the past, the only option for a woman with stress incontinence who wanted to avoid the long-term complications of the synthetic mesh slings was a pubovaginal sling. The rectus fascial harvester can be inserted through a small abdominal incision (e.g., about 3 cm to about 5 cm long) such that the dilator is positioned underneath the rectus fascia. Then using the integral cutter-stapler, similar to a pair of scissors, staple across the fascia and cut at the same time. In doing so, this would completely transect the segment of fascia about 2 cm wide by about 7 cm long, for example. However, other sizes segments of fascia can be harvested in some embodiments. For example, in some embodiments the segment of fascia may be in a range of about 1 cm to about 4 cm in width and in a range of about 4 cm to about 20 cm in length. This device would save roughly 25 to 30 minutes of operating time.

The rectus fascial harvester devices provided herein are convenient for a clinician operator to manipulate. The example device has a minimal number of working parts, such as a dilator that is round and can be premeasured to be a particular target diameter size, and that slips underneath a small incision of the rectus fascia. Then with the scissor-like handles, the cutter-stapler goes underneath or deep to the dilator, and transects and staples in one maneuver. Some of the benefits of this would be aiding in the speed of the surgery, and being able to provide the patient with an all-natural autologous sling that does not use any synthetic components.

Figure 1A:
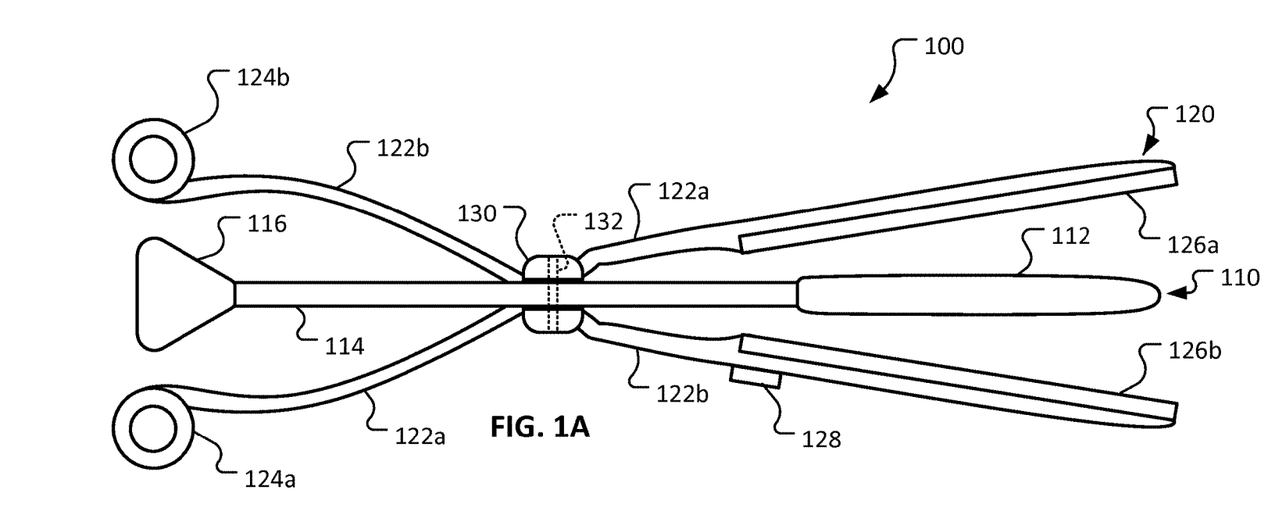
FIG. 1A is a top view of a fascial tissue harvesting device in accordance with some embodiments provided herein.
Figure 1B:
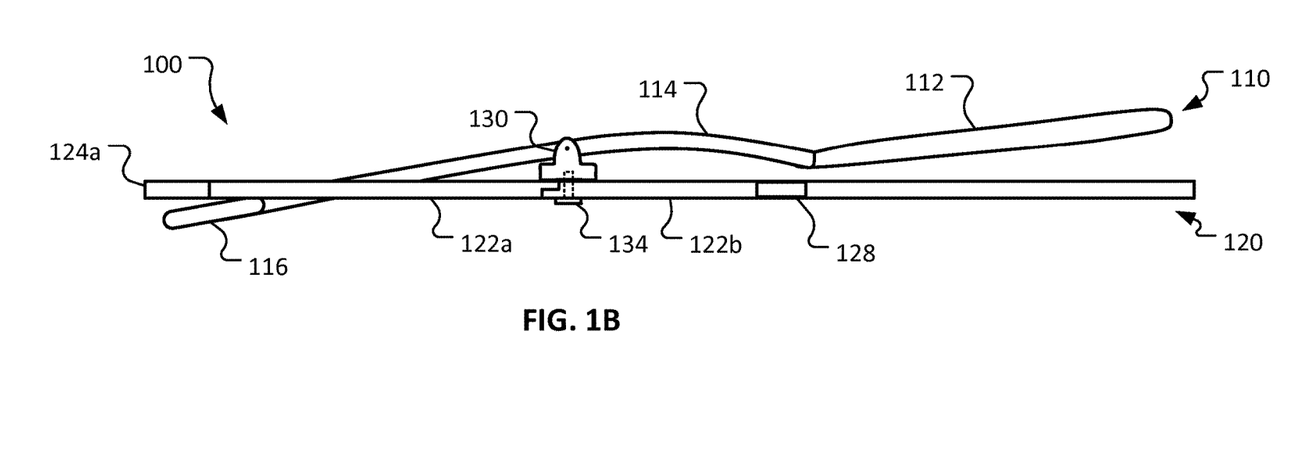
FIG. 1B is a side view of the fascial tissue harvesting device of FIG. 1A.

Referring to FIGS. 1A and 1B, an example rectus fascia harvester 100 includes a dilator 110, a cutter-stapler 120 and a connection hub 130. Dilator 110 is pivotably coupled to connection hub 130 using a pin 132. Cutter-stapler 120 is pivotably coupled to connection hub 130 using a pin 134.

In some embodiments, rectus fascia harvester 100 is comprised of biocompatible materials such as, but not limited to, surgical stainless steel (e.g., 316, 440, 420, etc.), titanium, polymeric materials, and combinations thereof.

Dilator 110 includes a distal working end 112, a shaft 114 and a grip end 116. In the depicted embodiment, working end 112 is generally cylindrical. In some embodiments, working end 112 may include curves or contours, or may have an ovular, flat, or other shaped cross-section. In some embodiments, the diameter of working end 112 is in the range of about 0.3 cm to about 0.9 cm, or about 0.7 cm to about 1.3 cm, or about 1.1 cm to about 1.7 cm, or larger than 1.7 cm. It should be understood that the width of the strip of tissue to be harvested is determined in part by the diameter of the working end 112.

Working end 112 is connected to proximal grip end 116 by shaft 114. In some embodiments, these parts can be cast, molded, or machined as a unitary construct. In some embodiments, these parts can be separately formed and then attached together (e.g., by welding, etc.).

Grip end 116 is shaped for convenient manual manipulation of dilator 110 by a clinician operator. In some circumstances, dilator 110 may need to have leverage applied thereto. Therefore, in some embodiments grip end 116 can be formed with a flat wide surface that is comfortable for the clinician to apply force to by hand.

In the depicted embodiment, cutter-stapler 120 is configured like a forceps or a scissors (e.g., in a scissor-arms arrangement). That is, cutter-stapler 120 is made of two pivotable components. Those two pivotable components are a first arm 122a and a second arm 122b. Each arm pivots in relation to each other about pin 134 that is coupled to connection hub 130. At least one of arm 122a and 122b includes a distal jaw end that is configured to cut and staple tissue therebetween. In the depicted embodiment, first arm 122a includes a first jaw end 126a, and second arm 122b includes a second jaw end 126b. Jaw ends 126a and 126b are configured to work cooperatively with each other to cut and staple tissue pinched between jaw ends 126a and 126b, when so actuated by the clinician.

In some embodiments, a sliding actuator 128 is coupled to at least one of the jaw ends 126a or 126b. Sliding actuator 128 is be a cutting device that the clinician manipulates to cut tissue that is positioned between jaw ends 126a and 126b. In some embodiments, other types of cutting devices are included. In some embodiments, the cutting device can be actuated from the handle end of rectus fascia harvester 100.

Jaw ends 126a and 126b are connected to proximal grip ends 124a and 124b by first arm 122a and second arm 122b respectively. In the depicted embodiment, grip ends 124a and 124b include finger holes, but in some embodiments, other types of user interface features can be included. For example, in some embodiments a clinician using a pistol grip, or a rotary adjustment, a sliding actuator, and the like, or a combination thereof can actuate jaw ends 126a and 126b. In some embodiments, some or all of the actuation aspects of rectus fascia harvester 100 are motorized.

In some embodiments, rectus fascia harvester 100 is configured to be articulable. That is, in some embodiments articulation joints can be included at or near to connection hub 130. As such, the clinician is afforded an increased capability to manipulate rectus fascia harvester 100. This feature may be advantageous, for example, for overweight patients.

Figure 2A:
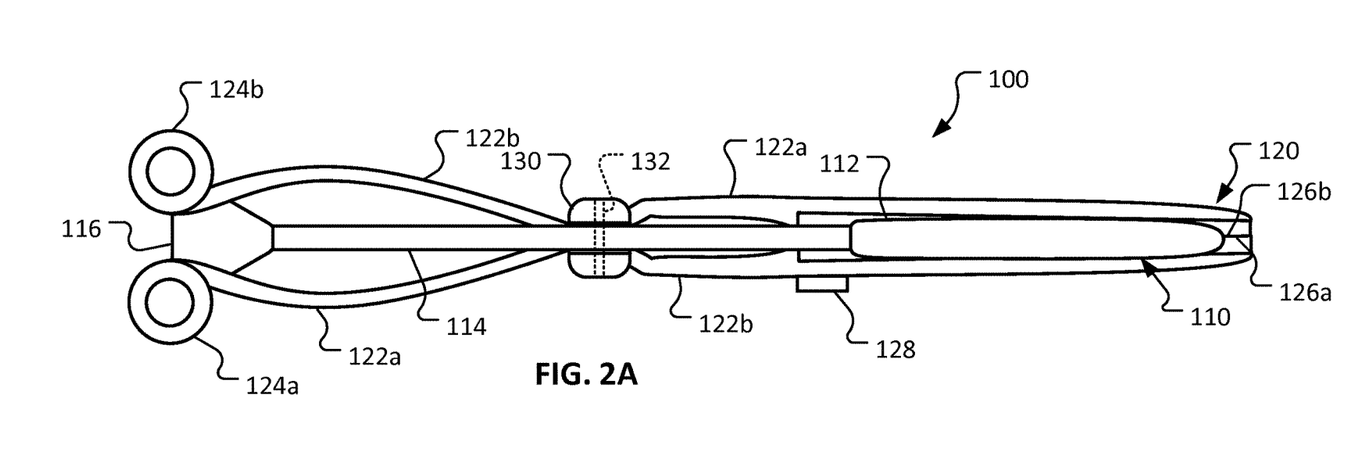
FIG. 2A is a top view of the fascial tissue harvesting device of FIG. 1A. In this figure, the fascial tissue harvesting device is configured in a different arrangement than the arrangement depicted in FIG. 1A.
Figure 2B:
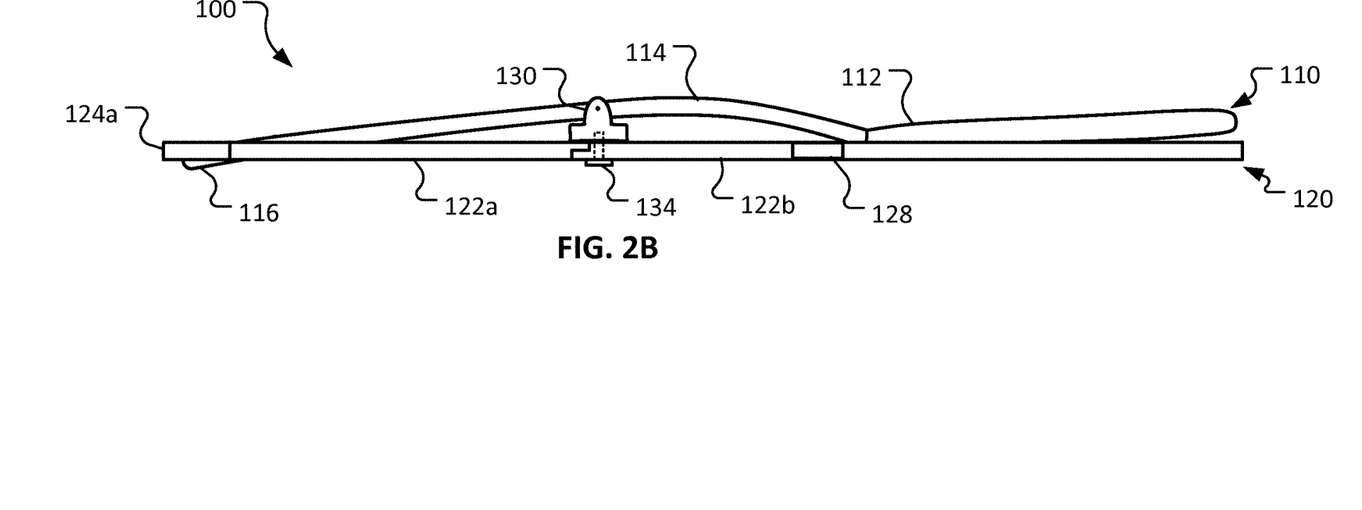
FIG. 2B is a side view of the fascial tissue harvesting device of FIG. 2A.

Referring now also to FIGS. 2A and 2B, rectus fascia harvester 100 is shown configured in a low profile arrangement such as could be used during insertion of rectus fascia harvester 100 through an incision in a patient's abdomen. In this arrangement, the distal tips of dilator working end 112 and jaw ends 126a and 126b are in close proximity to each other. Accordingly, the distal tip of rectus fascia harvester 100 can be inserted through a relatively small incision, such as an incision that is about 3 cm to about 5 cm long in some examples.

It should be understood that rectus fascia harvester 100 is intended to be used with the distal end portion of rectus fascia harvester 100 located internal to the patient and with the proximal end portion of rectus fascia harvester 100 located external to the patient. For example, at least grip end 116 and grip ends 124a and 124b remain external to the patient so that the clinician can manipulate grip end 116 and grip ends 124a and 124b.

When the distal end portion rectus fascia harvester 100 has been inserted through an incision, dilator working end 112 and jaw ends 126a and 126b are positioned on opposite sides of the rectus fascia. For example, dilator working end 112 can be position above the rectus fascia, while jaw ends 126a and 126b can be positioned below the rectus fascia. After the clinician has so oriented dilator working end 112 and jaw ends 126a and 126b in relation to the rectus fascia, rectus fascia harvester 100 may be oriented similar to the configuration shown in FIGS. 1A and 1B for example. The clinician then dilates the rectus fascia by gradually inserting rectus fascia harvester 100 into the patient's abdomen until the entire length of dilator working end 112 is in contact with rectus fascia tissue.

Figure 3A:
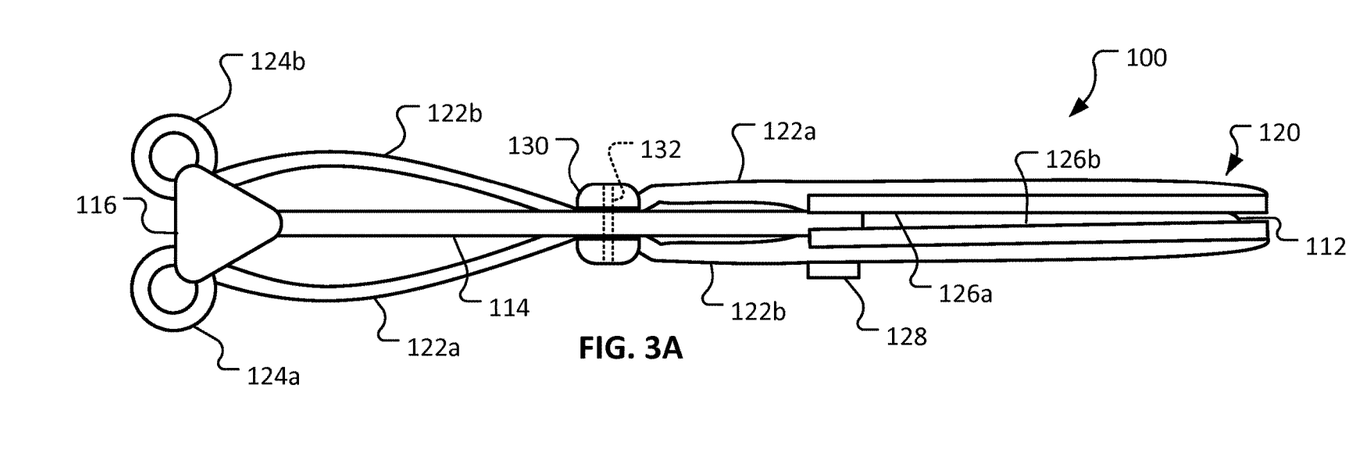
FIG. 3A is a top view of the fascial tissue harvesting device of FIG. 1A. In this figure, the fascial tissue harvesting device is configured in a different arrangement than the arrangements depicted in FIGS. 1A and 2A.
Figure 3B:
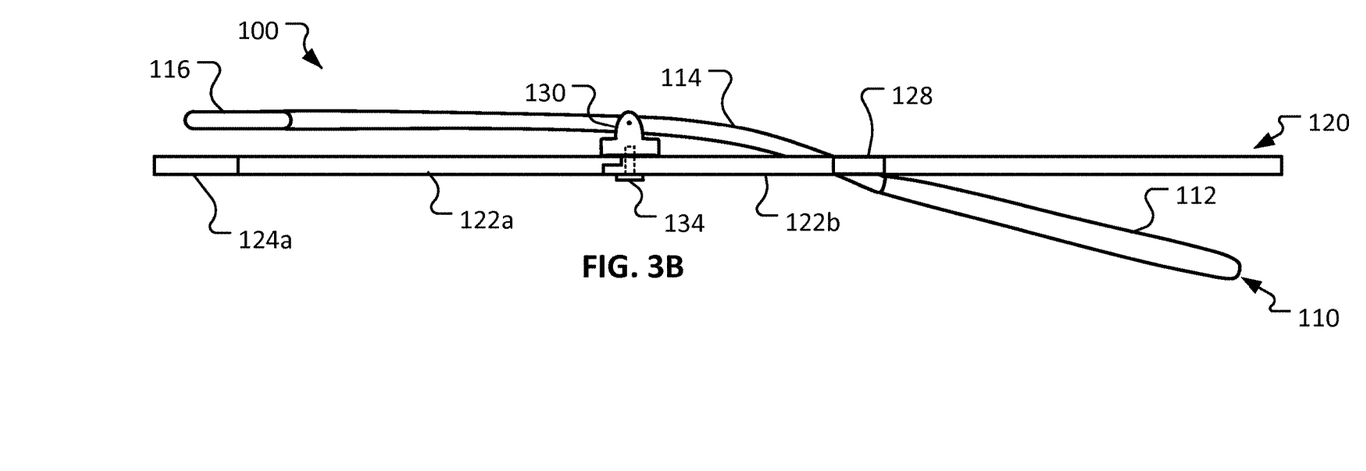
FIG. 3B is a side view of the fascial tissue harvesting device of FIG. 3A.

Referring now to FIGS. 3A and 3B, rectus fascia harvester 100 is shown with dilator working end 112 positioned below jaw ends 126a and 126b, and with jaw ends 126a and 126b closed together or nearly closed together. This configuration would be used when cutting and stapling the rectus fascia, as will be described further below.

From the foregoing description of rectus fascia harvester 100 in the context of FIGS. 1A, 1B, 2A, 2B, 3A, and 3B, it should be understood how rectus fascia harvester 100 can be manipulated by a clinician to attain the various configurations shown. Of course, rectus fascia harvester 100 can be manipulated into other beneficial configurations as well, as desired by the clinician.

Figure 4A:
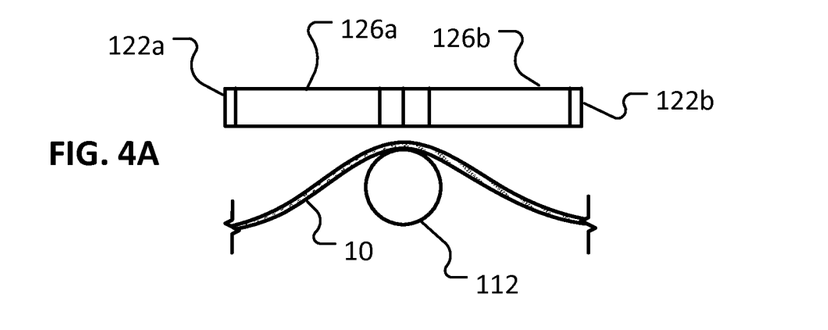
FIG. 4A is an end view showing the fascial tissue harvesting device of FIG. 1A in the process of dilating under abdominal wall (rectus) fascia.

FIGS. 4A-4D are a sequence of end views of a process of harvesting a rectus fascia 10 using example rectus fascia harvester 100. In FIG. 4A, rectus fascia 10 is being dilated by dilator working end 112. In this configuration, dilator working end 112 and jaw ends 126a and 126b are positioned on opposite sides of rectus fascia 10. More particularly, dilator working end 112 is position above rectus fascia 10, while jaw ends 126a and 126b are positioned below rectus fascia 10.

The distal ends of the first arm 122a (jaw end 126a) and the second arm 122b (jaw end 126b) collectively define a plane. Rectus fascia harvester 100 has a first configuration wherein the dilator working end 112 is disposed on a first side of the plane, and rectus fascia harvester 100 has a second configuration wherein the dilator working end 112 is disposed on a second side of the plane that is opposite to the first side of the plane.

Figure 4B:
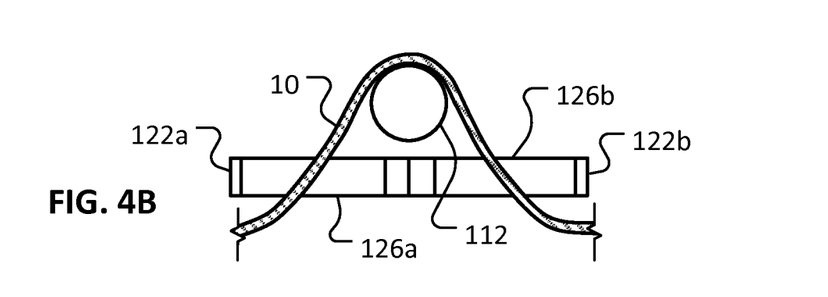
FIG. 4B is an end view showing the fascial tissue harvesting device of FIG. 1A being used to manipulate the rectus fascia into position to be transected.

When an entire length of dilator working end 112 is in contact with rectus fascia 10 as desired by the clinician, the clinician can manipulate dilator grip end 116 (refer to FIGS. 3A and 3B) to pivot dilator working end 112 below jaw ends 126a and 126b as depicted in FIG. 4B. In doing so, rectus fascia 10 is also pulled downward and below jaw ends 126a and 126b.

Figure 4C:
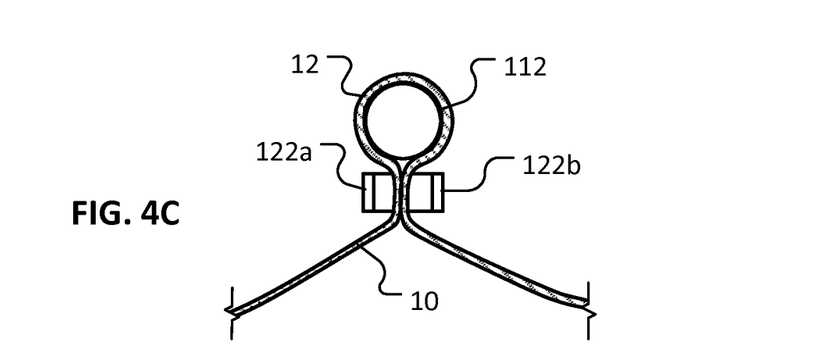
FIG. 4C is an end view showing the fascial tissue harvesting device of FIG. 1A with its jaws in position to staple and cut the rectus fascia.
Figure 4D:
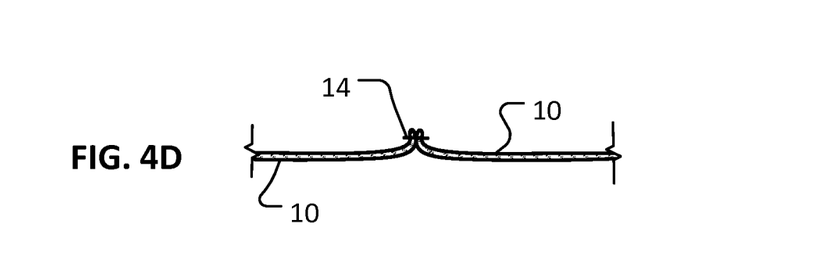
FIG. 4D is an end view showing the stapled rectus fascia after a strip of rectus fascia has been harvested using the devices and techniques provided herein.

Next, the clinician can manipulate grip ends 124a and 124b to pinch jaw ends 126a and 126b closed onto rectus fascia 10 as depicted in FIG. 4C. Rectus fascia harvester 100 may be orientated as shown in FIGS. 3A and 3B at this stage of the harvesting process. A rectus fascia portion 12 is positioned around dilator working end 112. Rectus fascia portion 12 will be harvested from the patient.

Lastly, the clinician can actuate rectus fascia harvester 100 so that jaw ends 126a and 126b staple rectus fascia 10 and cut rectus fascia 12 into a separate strip of tissue. Thereafter, rectus fascia harvester 100 and the strip of rectus fascia 12 can be removed from the patient. Remaining rectus fascia 10 is shown with installed staples 14 in FIG. 4D.

Figure 5:
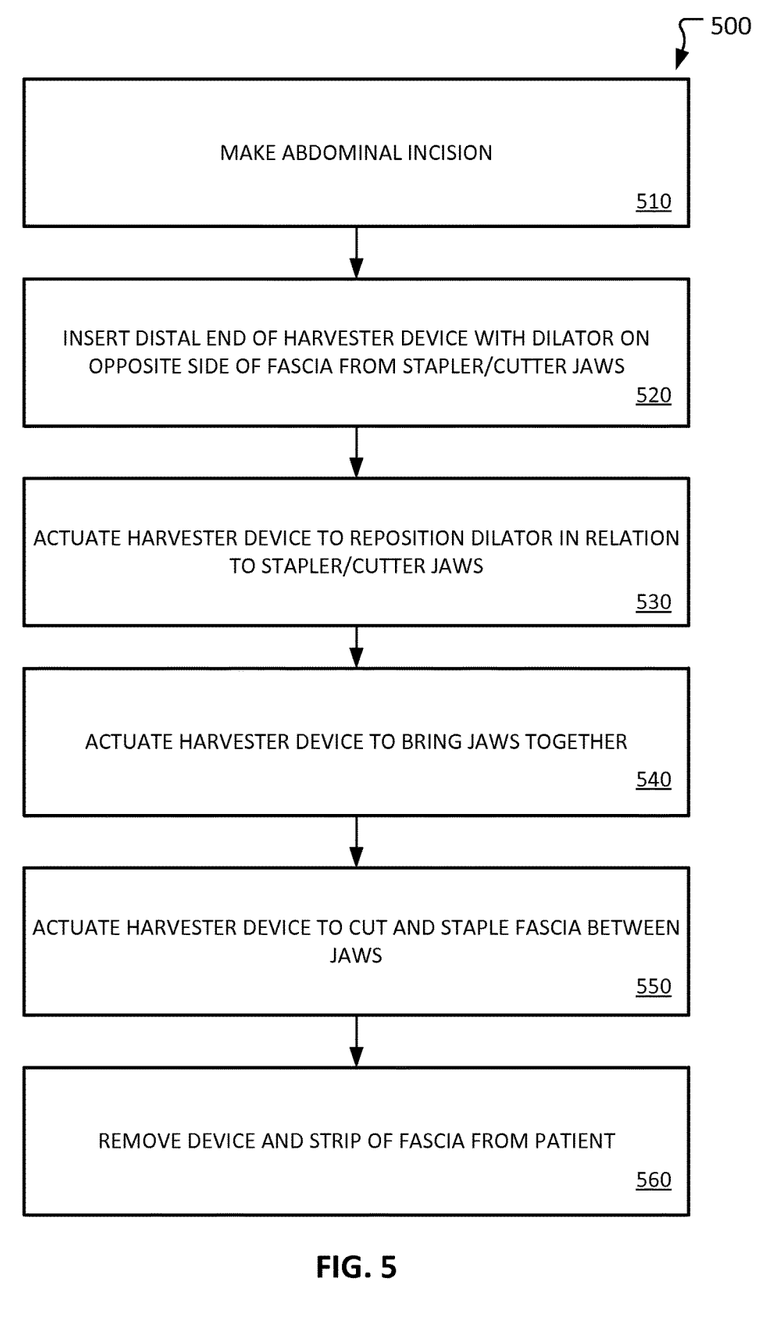
FIG. 5 is flowchart of a rectus fascia harvesting method in accordance with some embodiments provided herein.

Referring now to FIG. 5, a flowchart of a method 500 for harvesting a strip of rectus fascia is provided. Method 500 can be performed, for example, by a clinician that is operating a rectus fascia harvesting device such as rectus fascia harvester 100 described above. Method 500 is a minimally invasive procedure. That is, method 500 can be used to harvest a strip of rectus fascia while requiring only relatively small (e.g., about 3 cm to about 5 cm) incisions.

At operation 510, the clinician makes an abdominal incision. The abdominal incision is of sufficient size so as to allow the rectus fascia harvesting device to be inserted therethrough.

At operation 520, the distal end of the rectus fascia harvesting device is inserted through the incision. In some examples, the rectus fascia harvesting device may be configured in a low profile arrangement such as shown in FIGS. 2A and 2B to facilitate insertion of the rectus fascia harvesting device through the incision. The insertion is performed so that the dilator of the rectus fascia harvesting device is on the opposite side of the rectus fascia in comparison to the cutter-stapler jaws of the rectus fascia harvesting device. The clinician continues to insert the rectus fascia harvesting device until the entire length of the dilator is in contact with fascial rectus as desired.

At operation 530, the clinician actuates the rectus fascia harvesting device to reposition the dilator in relation to the cutter-stapler jaws (e.g., refer to FIG. 4B). At operation 540, the clinician actuates the rectus fascia harvesting device to bring the cutter-stapler jaws together and to pinch the rectus fascia therebetween as shown in FIG. 4C.

At operation 550, the clinician actuates the rectus fascia harvesting device to staple and cut the rectus fascia between the cutter-stapler jaws. At operation 560, the rectus fascia harvesting device and the separated strip of rectus fascia is removed from the patient. The patient's rectus fascia has been stapled together, while a strip of rectus fascia has been separated and removed. The staples can be biodegradable.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A device for harvesting a rectus fascia strip from a patient in a minimally invasive manner, the device comprising:
   a dilator including a working end, a grip end, and a shaft extending between the working end and the grip end, the working end being configured to dissect the rectus fascia;
   a cutter-stapler, the cutter-stapler including a first arm and a second arm, distal ends of at least one of the first arm and second arm configured to cut and staple the rectus fascia in response to being actuated; and
   a connection hub, the dilator being pivotably coupled to the connection hub, the first arm and the second arm being pivotably coupled to the connection hub.

2. The device of claim 1, wherein the working end is generally cylindrical.

3. The device of claim 1, wherein the dilator is pivotably coupled to the connection hub about a first pin.

4. The device of claim 1, wherein the dilator is comprised of stainless steel.

5. The device of claim 1, wherein a proximal portion of the dilator includes a grip end configured for manual manipulation by a clinician.

6. The device of claim 1, wherein the first arm and the second arm are pivotably coupled to the connection hub about a pin.

7. The device of claim 1, wherein the dilator is pivotably coupled to the connection hub about a first pin, wherein the first arm and the second arm are pivotably coupled to the connection hub about a second pin, and wherein the first pin is perpendicular to the second pin.

8. The device of claim 1, wherein the distal ends of the first arm and the second arm define a plane, wherein the device has a first configuration wherein the working end of the dilator is disposed on a first side of the plane, and wherein the device has a second configuration wherein the working end of the dilator is disposed on a second side of the plane that is opposite to the first side of the plane.

9. The device of claim 8, wherein the device is reconfigured between the first and second configurations by pivoting the dilator about the connection hub.

10. The device of claim 1, wherein a proximal portion of the first arm and a proximal portion of the second arm are configured for manual manipulation by a clinician.

11. The device of claim 1, wherein the first arm and the second arm are configured to pivot in relation to each other in a scissor-arms arrangement.

12. A method for harvesting a rectus fascia strip from a patient in a minimally invasive manner, the method comprising:
    incising an abdomen of the patient to create an incision;
    inserting a distal portion of a rectus fascia harvesting device through the incision, the rectus fascia harvesting device comprising:
      a dilator including a working end, a grip end, and a shaft extending between the working end and the grip end, the working end being configured to dissect the rectus fascia;
      a cutter-stapler, the cutter-stapler including a first arm and a second arm, distal ends of at least one of the first arm and second arm configured to cut and staple the rectus fascia in response to being actuated; and
      a connection hub, the dilator being pivotably coupled to the connection hub, the first arm and the second arm being pivotably coupled to the connection hub;
    dilating, using the working end, the rectus fascia;

actuating the rectus fascia harvesting device to position the rectus fascia between the distal ends of the first arm and second arm;

actuating the rectus fascia harvesting device to install a plurality of staples and to cut the rectus fascia to create a strip of harvested rectus fascia; and removing the rectus fascia harvesting device and the strip of harvested rectus fascia from the patient.

13. The method of claim 12, wherein the inserting includes positioning, on opposite sides of the rectus fascia, (i) the working end and (ii) the distal ends of the first arm and the second arm.

14. The method of claim 12, wherein the inserting includes placing an entire length of the working end in contact with the rectus fascia.

15. The method of claim 12, wherein the actuating the rectus fascia harvesting device to position the rectus fascia between the distal ends of the first arm and second arm includes pinching the rectus fascia between the distal ends of the first arm and second arm.

16. The method of claim 12, wherein the strip of harvested rectus fascia is about 1 cm to about 4 cm in width.

17. The method of claim 12, wherein the plurality of staples are biodegradable.

18. The method of claim 12, wherein the inserting includes positioning, on opposite sides of the rectus fascia, (i) the working end and (ii) the distal ends of the first arm and the second arm, and wherein the actuating the rectus fascia harvesting device to position the rectus fascia between the distal ends of the first arm and second arm includes pinching the rectus fascia between the distal ends of the first arm and second arm.

* * * * *